United States Patent
De La Maza Rivera et al.

(10) Patent No.: US 9,675,555 B2
(45) Date of Patent: Jun. 13, 2017

(54) LIPOSOME-ENCAPSULATED BICELLES AND USE THEREOF IN DILUTED SYSTEMS

(75) Inventors: Alfons De La Maza Rivera, Barcelona (ES); Olga López Serrano, Barcelona (ES); Gelen Rodríguez Delgado, Barcelona (ES); Laia Rubio Toledano, Barcelona (ES); Lucyana Barbosa, Barcelona (ES); Guadalupe Soria Rodríguez, Barcelona (ES); Ana María Planas Obradors, Barcelona (ES); Mercedes Cocera Núñez, Barcelona (ES)

(73) Assignee: CONSEJO SUPERIOR DE INVESTIGACIONES CIENTIFICAS (CSIC), Madrid (ES)

( * ) Notice: Subject to any disclaimer, the term of this patent is extended or adjusted under 35 U.S.C. 154(b) by 874 days.

(21) Appl. No.: 13/582,328

(22) PCT Filed: Feb. 28, 2011

(86) PCT No.: PCT/ES2011/070128
§ 371 (c)(1),
(2), (4) Date: Aug. 31, 2012

(87) PCT Pub. No.: WO2011/107643
PCT Pub. Date: Sep. 9, 2011

(65) Prior Publication Data
US 2012/0321683 A1    Dec. 20, 2012

(30) Foreign Application Priority Data

Mar. 1, 2010 (ES) .................................. 201030298

(51) Int. Cl.
*A61K 9/127* (2006.01)

(52) U.S. Cl.
CPC .................................... *A61K 9/127* (2013.01)

(58) Field of Classification Search
CPC ...................................................... A61K 9/127
(Continued)

(56) References Cited

U.S. PATENT DOCUMENTS

| 7,368,129 B1 * | 5/2008 | Aneja .................. A61K 9/1271 264/4.1 |
| 2002/0061331 A1 * | 5/2002 | Zasadzinski et al. ........ 424/451 |

(Continued)

OTHER PUBLICATIONS

Kisak E. T. et al in Current Medicinal Chemistry, 2004, vol. 11, pp. 199-219.*

(Continued)

*Primary Examiner* — Gollamudi Kishore
(74) *Attorney, Agent, or Firm* — Squire Patton Boggs (US) LLP

(57) ABSTRACT

The aim of the invention is to preserve the morphology of bicelles in high-water-content environments. For this purpose, the invention relates to a liposome comprising, in its internal aqueous medium, at least one bicelle. The bicelles concentration in said aqueous means is between 5 and 25% dry weight in relation to the end liposome. The invention also relates to the use of said liposomes for the encapsulation of active principles, as well as to the use thereof as a medicament or to produce a cosmetic product. The invention further relates to the method for obtaining said liposomes.

19 Claims, 7 Drawing Sheets

(58) Field of Classification Search
USPC .......................................................... 424/450
See application file for complete search history.

(56) References Cited

U.S. PATENT DOCUMENTS

| | | | | |
|---|---|---|---|---|
| 2005/0175684 | A1* | 8/2005 | Gwathmey | A61K 9/0019 424/450 |
| 2008/0292688 | A1* | 11/2008 | Wang | A61K 8/14 424/450 |
| 2010/0015218 | A1* | 1/2010 | Jadhav | C12N 15/88 424/450 |
| 2011/0105995 | A1* | 5/2011 | Zhu et al. | 604/20 |
| 2011/0250639 | A1* | 10/2011 | Ernst et al. | 435/69.1 |
| 2014/0271814 | A1* | 9/2014 | Andrali | A61K 9/1271 424/450 |

OTHER PUBLICATIONS

L. Barbosa-Barros, et al.; Effect of bicellar systems on skin properties; Science Direct; International Journal of Pharmaceutics 352 (2008) pp. 263-272; Oct. 22, 2007.

Jesper Lind, et al.; Lipid Dynamics in fast-tumbling bicelles with varying bilayer thickness; Effect of model transmembrane peptides; Science Direct; Bochimica et Biophysica Acta 1778 (2008) pp. 2526-2534; Jul. 22, 2008.

L. Rubio, et al.; Bicellar systems for in vitro percutaneous absorption of diclofenac; Science Direct; International Journal of Pharmaceutics 386 (2010) pp. 108-113; Nov. 14, 2009.

Jennifer A. Whiles, et al.; Bicelles in structure-function studies of membrane-associated proteins; Bioorganic Chemistry 30(2002) pp. 431-442; Jan. 30, 2002.

Gelen Rodriguez et al.; Bicosomes: Bicelles in Dilute Systems; Biophysical Journal vol. 99 Jul. 2010 pp. 480-488; Mar. 31, 2010.

Gelen Rodriguez et al.; Conformational Changes in Stratum Corneum Lipids by Effect of Bicellar Systems; Langmuir Article; pp. 10595-10603; Jun. 17, 2009.

L. Barbosa-Barros et al.; Penetration and Growth of DPPC/DHPC Bicelles Inside the Stratum Corneum of the Skin; Langmuir 2008, 24, pp. 5700-5706; Mar. 6, 2008.

L. Barbosa-Barros et al.; Lipid Nanostructures: Self-Assembly and Effect on Skin Properties; molecular pharmaceutics, vol. 6, No. 4, pp. 1237-1245; May 11, 2009.

Lucyanna Barbosa-Barros et al.; Structural Versatility of Bicellar Systems and Their Possibilities as Colloidal Carriers; pharmaceutics 2011, 3, pp. 636-664; Sep. 14, 2011.

Katsaras, John, et al., "Bicellar" lipid mixtures as used in biochemical and biophysical studies, Naturewissenchaften (2005) 92: 355-366 (12 pages).

Nieh, Mu-Ping, et al., Structural Phase Behavior of High-Concentration, Alignable Biomimetic Bicelle Mixtures, Macromol. Symp. 2005, 219, pp. 135-145 (12 pages).

Rodriguez, Gelen, et al., Bicosomes: Bicelles in Dilute Systems, Biophysical Journal, vol. 99, Jul. 2010, pp. 480-488 (9 pages).

Barbosa-Barros, L., et al., Lipid Nanostructures: Self-Assembly and Effect on Skin Properties, Molecular Pharmaceutics, vol. 6, No. 4., pp. 1237-1245 (9 pages).

Lopez, Olga, et al., Direct formation of mixed micellese in the solubilization of phospholipid liposomes by Triton X-100, FEBS Letters 426 (1998) pp. 314-318 (5 pages).

Evans, Cara, et al., Encapsulating Vesicles and Colloids from Cochleate Cylinders, Langmuir 2003, 19, pp. 3109-3113 (5 pages).

Suga, Keishi, et al., Liposomes destabilize tRNA during heat stress, Biotechnology Journal, 2010, 5, pp. 526-529 (4 pages).

Barbosa-Barros, L., et al., Penetration and Growth of DPPC/DHPC Bicelles Inside the Stratum Corneum of the Skin, Langmuir 2008, 24, pp. 5700-5706 (7 pages).

Marcotte, Isabelle, et al., Bicelles as Model Membranes for Solid- and Solution-State NMR Studies of Membrane Peptides and Proteins, Concepts in Magnetic Resonances Part A., vol. 24A(1), pp. 17-37 (21 pages).

Sanders, Charles R., et al, Bicelles: a model membrane system for all seaons?, Ways & Means (8 pages).

Whiles, Jennifer A., et al., Bicelles in structure-function studies of membrane-associated proteins, Bioorganic Chemistry 30 (2002) pp. 431-442 (12 pages).

Takajo, Yuichi, et al., Structure and morphological transition of long-chain phospholipid vesicles induced by mixing with short-chain phospholipid, Colloids an dSurfaces B: Biointerfaces 76 (2010) pp. 571-576 (6 pages).

Benson, Heather A.E., Transdermal Drug Delivery: Penetration Enhancement Techniques, Current Drug Delivery, 2005, 2, pp. 23-33 (11 pages).

Durr, Ulrich H.N., et al., When detergent meets bilayer: Birth and coming of age of lipid bicelles, Progress in Nuclear Magnetic Resonance Sprectroscopy 69 (2013) pp. 1-22 (22 pages).

Leupold, Eik, et al., Apolipoprotein E peptide-modified colloidal carriers: The design determines the mechanism of uptake in vascular endothelial cells, Biochimica et Biophysica Acta 1788 (2009), pp. 442-449 (8 pages).

Mineev, K.S., et al., Dimeric Structure of the Transmembrane Domain of Glycophorin A in Lipidic and Detergent Environments, Acta Naturae, vol. 3 No. 2(9) 2011, pp. 90-98 (9 pages).

Rapoport, Natalya, Ultrasound-mediated micellar drug delivery, International Journal of Hyperthermia, vol. 28 (4) 2012, pp. 374-385 (13 pages).

* cited by examiner

LIPOSOME-ENCAPSULATED BICELLES AND USE THEREOF IN DILUTED SYSTEMS

The aim of the invention is to preserve the morphology of bicelles in high-water-content environments. For this purpose, the invention relates to a liposome comprising, in its internal aqueous medium, at least one bicelle. The bicelles concentration in said aqueous means is between 5 and 25% dry weight in relation to the end liposome. The invention also relates to the use of said liposomes for the encapsulation of active principles, as well as to the use thereof as a medicament or to produce a cosmetic product. The invention further relates to the method for obtaining said liposomes.

BACKGROUND

Liposomes have been the object of many investigations due to its potential use for the microencapsulation of medicament and its application in cosmetics and in clinical application (Teschke, O.; de Souza, E. F. *Langmuir* 2002, 18, 6513).

A liposome is a spherical hollow vesicle comprising mainly phospholipids which consists in an hidrosoluble head and a liposoluble tail, organized in twin layers. The lipophilic tails of phospholipids contact each other forming a double layer web which is hydrophilic in its external sections and lipophilic in its internal portion, said web enclosing an aqueous internal mass.

At present liposomes are used as carriers of various substances between the external part and the internal part of the cell due to the fact that they are the most efficient carriers to introduce substances within the cells, with a broad field of applications. Some of the substances are medicaments or cosmetics and they are even used in biotechnology, in some cases for genetic therapy, to introduce gens of an organism within a different organism.

The use of these structures as carriers has the advantage that they may be programmed in order that the medicament is capable to be released during a long period of time. Furthermore, they have a natural tendency to bind to cells and tissues obtaining the highest therapeutic efficiency and minimizing unwanted side effects. Thus, the liposomes bounded to antibodies, bind to target cells easier than the soluble forms of antibodies. From the chemical point of view, they are similar to cells circulating within the blood with which they are compatible and in the other side they constitute a useful protection method for protecting labile products due to the fact that they are not affected by degradation so that they perform efficiently.

Other reported applications attributed for these structures are as follows: to target immunomodulating agents to the cells of the immune system; controlled release of medicaments against systemic type infections, to reduce the side effects of some medicaments, as well as diagnosis methods or substitutes for blood cells.

However, the use of liposomes as carriers is not limited only to the health field, as in the textile industry the microencapsulation is a new technology which permits to substitute the dispersions or emulsions of certain substances by similar fluids in which said components are dispersed within microcapsules of inert substances, which bind to the textile material by an effective system. The final properties conferred to the textile substrate originate from the type of encapsulation carried out and the release mechanism obtained. Up to now at industrial level, the production of biofunctional tissues (smart tissues) has followed an empirical development route based on the system of "trial and error". However, this process requires an efficient physico-chemical knowledge of the interactions existing at the level of fibre-microcapsule. In the contrary case, it is not possible to optimize the application technology nor to control the release of the active principle. In this sense, liposomes are being used as microencapsulating substances in industrial processes for wool dyeing (Marti, M. et al. *Textile Res. J.* 2001, 71(8), 678-682; Marti, M. et al. *Inter. Textile Bull.* 2003, 2, 60-64; Marti, M. et al. *Text. Res. J.* 2004, 74(11), 961-966).

These liposomal structures, with diameters comprised between 100 nm and 1 µm have the drawback that they are too large to pass through the skin in transdermal applications.

On the other side, bicelles are disc-like nano-structures composed by a long chain phospholipid located in the centre of a flat bilayer area and a short chain phospholipid located on the edges (Sanders, C. R.; Hare, B. J.; Howard, K. P.; Prestegard, J. H. *Prog. NMR Spectroscopy* 1994, 26, 421). The characteristic of these systems, formed only by lipids, of organizing in twin layers and its characteristic to align to a magnetic field, has permitted its ample use as patterns for webs in different investigations of the structure of webs of proteins and peptides (Sanders, C. R.; Prestegard, J. H. *Biophys J.* 1990, 58, 447).

Recently, it has been proposed the use of bicelles in dermatologic applications due to its small size which is sufficient to pass through the skin. These investigations have evidenced that the action of the bicelles on the skin barrier depends on different composition variables which act as permeating agents in the skin or reinforcing agents for the lipidic structures (Barbosa-Barros, L.; Barba, C.; Cócera, M.; Coderch, L.; López-Iglesias, C.; de la Maza, A.; López, O. *Inter. J. Pharmaceut* 2008, 352, 263). In addition to the use of bicelles for the improvement of the skin, it is now under investigation the possibility that bicelles incorporate medicaments and other bioactive compounds.

The problem which arises when working with bicelles is that they adopt different morphologies depending on the molar rate between the long chain and the short chain phospholipids; the total concentrations of phospholipids and the temperature. Thus, as an example, in conditions of a high dilution, the small disc-like bicelles are transformed into big structures, such as vesicles, layers, rod-like micelles, etc. This behaviour could hinder the application of these systems by the systemic route due to the fact that the properties of the bicelles will be affected by dilution and the damage that these structures could generate has not yet been well defined.

A method for the stabilization of the structure of the bicelles in high dilution conditions would consist in its development starting from blends of lipids conjugated to poliethylenglycol (PEG-lipids). The problem in this method is that the obtained bicelles lose some of its characteristics, as for example, the capacity to enhance its permeability.

Therefore, a problem still persists in the stabilization of the structure of bicelles in diluted environments.

DETAILED DESCRIPTION

With the aim to maintain the size and form of the small disc-like bicelles, the present invention provides a method for its encapsulation within lipidic vesicles or liposomes.

In high dilution conditions, the bicelle nanostructures lose its morphology becoming spherical vesicles with much larger sizes, such that this behaviour could hinder the use of these compounds by means of the systemic route, in which the water content is very high.

However, in diluted environments, liposomes are morphologically stable acting therefore as good carriers for systemic applications, giving ground to a method useful for the stabilization of the morphology of the bicelles.

Therefore, the present invention refers to new lipidic structures which combine the properties of its components: liposomes and bicelles. They are lipidic systems formed by an external phospholipidic web forming a vesicle which internally contains disc-like structures which are also lipidic.

In this connection, one aspect of the present invention refers to a liposome comprising in its aqueous internal solution at least one bicelle.

In one preferred embodiment of this invention, a liposome has a bicelle concentration between 5 and 25% of the dry weight in respect to the final liposome. The concentration of bicelles is expressed therefore in percentage in dry weight in respect to the dry weight of the final liposome, that is, of the liposome comprising said bicelle.

It is assumed that the liposome is formed by an external vesicle (structurally very resistant in respect to changes in the environment) having as function to isolate and protect the bicelles contained in its internal part (disc-like structures, very versatile and modulatable) permitting in this way to maintain its form and size in order that they may be used in applications which are to be administrated through different routes in which the water content is very high as for example, without limitation, the digestive tract, parenteral route, respiratory route and topic route.

Bicelles are structures very sensible to the changes in the environment in which they reside for which reason the isolation of these structures protects them against eventual variations. Said isolation is carried out by means of the encapsulation of said bicelles within lipidic vesicles or liposomes, in which the external lipidic web of the liposome ensures the isolation and stability of the bicelle contained in its internal part. That is, within the lipidic vesicle a perfect microenvironment is created so that the bicelles may conserve its morphology all the time. Additionally, the liposomes yield the advantage of being stable as to the temperature and dilution in comparison with non encapsulated bicelles.

One of the most interesting properties of the bicelles is their capacity to enhance permeability in order to pass through the various physiological barriers as the hematoencephalic barrier, the barrier formed by the horny stratum of the skin, different mucous webs as for example, without limitation, oral, gastric, intestinal, nasal, conjuntival, pulmonary and other physiologic barriers.

Said permeating effect of the bicelles is due to its small size and composition (long chain phospholipids and short chain phospholipids with surface activating effect or surface active effect) and it is originated because the lipids of the bicelles when mixed with the lipids of the webs of the tissues modify its fluidity and permeability.

The capacity to enhance permeability of different biologic barriers (as the hematoencephalic barrier, the barrier formed by the horny stratum of the skin, different mucous web, as for example, but without limitation, oral, gastric, intestinal, nasal, conjuntival, pulmonary and other physiological barriers) and therefore the passage through these barriers provides to the bicelles a substantial advantage for its application in the medicine and pharmacy fields.

The temperature together with the hydration are key parameters in the determination of the structure which will adopt a bicelle and therefore they are very important for the correct formation of the above described liposome.

When the total lipid concentration is modified, morphologic changes are induced in the structure of the bicelle provoked by the variation in the water content. When the water content increases, the concentration of phospholipids in water diminishes, being removed from the structure of the bicelles (mainly from the ends) to be released in the water in form of monomers. This fact and the high hidrophobocity of the phospholipid long chain molecules composing the bicelle induce an increase in the molar ratio (q) between the long chain phospholipid and the short chain phospholipid and, as a consequence, an increase in the diameter of the bicelles.

At a concentration of 20% of lipidic content, the bicelles are small disc-like structures (smaller than 10 nm) while when increasing water content in the system the small structures transform into aggregates of bigger size, so that for a lipid concentration of 0.62% structures are beginning to be detected with sizes of 500 nm mixed with smaller aggregates and for lipidic concentrations of 0.15% only very sizable structures bigger than 500 nm are detected, for which reason the bicelle has preferably a total concentration of the lipidic content of 20%.

According to another preferred embodiment, the average transition temperature of the lipids of the above described liposome is comprised between 4 and 40° C.

In the present invention, the term "phase transition temperature", Tm, refers to the temperature in which the system passes from the gel phase to the liquid crystal phase. Two different Tm will have to be taken into account, the Tm of the lipids forming the liposome and the Tm of the lipids forming the bicelle. Even though the bicelles are formed by a mix of two types of lipids, it will be considered as the phase transition temperature for bicelles, the temperature corresponding to the long chain phospholipid, given the fact that this latter is responsible for the formation of the twin layer in the structure and the phase transition to which we refer is necessarily bound to the formation of twin layers. The term "average transition temperature" refers to the range of temperatures in which the Tm of the bicelle and the Tm of the liposome coincide and therefore the range of temperatures in which the above described liposome keeps stable.

Taking into account that the Tm for the lipids of the liposome is comprised between −20° C. and 40° C. and that the Tm of the lipids within the bicelle is comprised between 4° C. and 60° C., the average transition temperature of the above described liposome is comprised within the range of 4° C. to 40° C.

In another preferred embodiment, the bicelle contained within the liposome comprises long chain phospholipids in its flat central portion and short chain phospholipids in the end portions.

Each one of the phospholipids contained within the bicelle is formed by glycerol to which two fatty acids and a phosphate group are bound. As above stated, according to the location of the phospholipids in the bicelle we will find that the fatty acid chain will be longer or shorter. Thus, the phospholipids located in the flat central portion must have a fatty acid chain having 12 carbon atoms as a minimum, preferably a minimum of 15 carbon atoms and more preferably 18 carbon atoms as a minimum, while the fatty acid chain of phospholipids located at the ends will have a length as a maximum of 8 carbon atoms, preferably a maximum of 7 carbon atoms, and still more preferably a maximum of 5 carbon atoms.

FIG. 1 illustrates the form in which the phospholipids are located in the bicelle according to the length of its hydrocarbon chain.

In a more preferred embodiment, the ratio of the molar concentrations of long chain phospholipids to short chain phospholipids of the bicelle is comprised between 1 and 10, preferably between 1.5 and 9, and more preferably between 2 and 8.

In other still more preferable embodiment the difference between the number of carbon atoms between the long chain phospholipids and the short chain phospholipids of the bicelle is comprised between 5 and 25, preferably between 7 and 22, and more preferably between 8 and 20.

As above stated, a meaningful difference between the number of carbon atoms of the different phospholipids composing the bicelles provides this structure with the capacity to increase the permeability to pass through different physiologic barriers, as for example the barrier for the horny stratum of the skin or the hematoencephalic barrier.

Due to the fact that the composition of the phospholipidic bilayer sets conditions to multiple parameters to be taken into account as the packing density, flexibility, osmothic strength, stability "in vivo" and "in vitro", permeability, electrical load, antigenic capacity, etc., the long chain phospholipids used in the development and production of bicelles may be selected, without limitation, within the list comprising dilauryl-phosphatidylcholine (DLPC), dimyristoyl-phosphatidylcholine (DMPC), dipalmitoil-phosphatidylcholine (DPPC), distearyl-phosphatidylcholine (DSPC) and diarilquidonil-phosphatidylcholine (DAPC), being preferable DMPC and DPPC and still more preferable DPPC. In the same manner, the short chain phospholipid used in the development and production of bicelles may be selected, without limitation, within the list comprising dipentanoil-phosphatidylcholine (DPePC), dihexanoil-phosphatidylcholine (DHPC), diheptanoil-phosphatidylcholine (DHpPC) and dioctanoil-phosphatidylcholine (DOcPC), being dihexanoil-phosphatidylcholine (DHPC) preferable.

In a preferred embodiment, the bicelle has a length of the major axis comprised between 10 and 80 nm, more preferable between 15 and 75 nm and, in another preferred embodiment, the liposome has a diameter comprised between 200 and 1000 nm, more preferable between 220 and 900 nm.

In the following, to refer to any liposome described in previous paragraphs, the term "liposome of the invention" may be employed.

Another aspect of the present invention refers to the composition which comprises the liposome of the invention, which will be called in the following "composition of the invention".

The results of the invention confirm that the encapsulation of the bicelles forming the liposome of the invention preserve its structure in dilution conditions. Consequently, if we add the properties of said structures, the use of the liposomes of the invention would be a good strategy both for ensuring the stability of the bicelles in all biological tissues, due to the fact that in the majority of them have a high content of water, as well as for introducing bicelles by means of biological fluids with high water content, as for example, without limitation, cerebrospinal fluid, blood and/or saliva.

On the other side, the liposomes of the invention have the capacity to encapsulate different substances in a similar way as the liposomes do, however, with the advantage that after the transportation of the medicament, the penetration of the same within a given tissue will be enhanced by the effect of the internal disc-like structure of the bicelle. Furthermore, the encapsulation and transport of hidrophobic substances within the liposomes of the invention is enhanced by the fact that these structures contain a higher range of bilayer than the liposomes. Thus, the substances may be incorporated into the bicelles, so that these structures may be used as carriers, markers or for any other application which may be considered suitable according to the experts in the matter.

As above described, microencapsulation in the textile field is a new technology which permits to substitute dispersions or emulsions of certain substances by similar fluids, wherein said components are dispersed within the microcapsules of inert substances which are bound to the textile product by means of any effective system. The liposomes have been tested as microencapsulating agents, however due to the fact that this process requires an efficient physical-chemical knowledge of the interactions existing at the level of fibre-microcapsule, the liposomes of the invention are capable to improve in a substantial way the present applications of the liposomes in industrial processes for the dyeing of wool or any other textile material, increasing the adsorption, penetration and setting both of dyes or pigments as well as other substances used in this field of the technique, known to any expert on the matter, permitting to obtain fabrics capable of carrying out different functions which are presently named as "polifunctional fabrics" or "smart textiles".

Therefore, another aspect of the present invention refers to the liposome of the invention which contains additionally a dye and/or a pigment, as well as its use for the encapsulation of dyes, pigments and other substances used in this field of the technique, known to any expert on the matter and which permits to obtain fabrics which are capable of carrying out different functions, presently known as "polifunctional fabrics" or "smart textiles". Those liposomes of the invention which are capable of additionally containing dyes and/or pigments, may be used for the dyeing of biological fibers or textile materials or they may contain other substances used in the textile industry increasing the efficiency of the dyeing processes of said textile materials.

Another aspect of this invention refers to the liposome of the invention comprising additionally an active principle, as well as its use for the encapsulation of at least one active principle.

The term "active principle" refers to any substance which is capable to provoke an effect on the organism or to any substance which is capable to be used for identification or diagnosis. The activity of an active principle changes due to the nature of the active principles, however it is always related with the quantity which has been ingested or absorbed.

Thus, the active principle may be selected from a list comprising, without limitation, marker agents to be used as diagnostic means such as derivates of gadolinium (gadopenthetic acid, gadodiamine, gadotheric acid and gadotheridol) iron derivates (iron III ammonium citrate, "ferrumoxide" and iron III oxide) or derivates of magnesium, anti-inflammatory agents such as diclophenac, acetominophene or flufenamic acid; antioxidants such as polyphenols (flavonoids), vitamins (A, E, C), oligoelements (seleniun, zinc), caroteonids (luteine), aminoacids (teanin) or caffeine; sun filters as aminobenzoates, salicilates, benzophenones, derivates of dibenzoylmethane, cinamates or acrylates; citotoxic agents such as alquilanting agents, methotrexate, 6-mercaptopurine, 5-fluoroacile, antitumor antibiotics or cisplatin and derivates; immunogenic agents; substances bringing an exogenous contribution for pathologic situations of deficiency such as vitamins, iron, calcium, epidermic lipids with special importance for barrier function in the skin, such as ceramides, cholesterol sulfate or free fatty acids; nucleic acids or hydrophobic medicaments or blends of any of the above.

In a preferred embodiment, the active principle may be selected from diclofenac, iron, gadodiamide, flufenamic acid, caffeine, ceramides or cholesterol sulfate.

This invention brings evidence to the fact that substances like gadodiamide (useful as marker in image magnetic resonance permitting the continuous follow-up of the route of the liposomes of the invention inside the organism), dichlophenac and flufenamic acid (high performance antiinflamatory substances), iron (currently used for the treatment of anemia), caffeine (used as anti-oxidant) and ceramides and cholesterol sulfate (lipids responsible for the correct barrier function of the skin and involved in different biologic mechanisms) are efficiently encapsulated within the bicelles contained within the liposomes of the invention.

This capacity to use the liposomes of the invention as active pharmacologic vehicles could lead to the use of these structures for the preparation of medicaments for the treatment of disturbances related with the substance being transported, being appropriate for the treatment, among others, of pathologies related with inflammatory processes (when antiinflammatory substances such as dichlofenac and flufenamic acid are encapsulated), disturbances related to the deficiency of iron and/or B12 vitamin, such as anemia and Crohn illness among others, injuries (by the regulation of the adhesion of platelets), cancer (encapsulation of citotoxic agents), etc.

Additionally, the liposomes of the invention could be used as well in genic therapy targeting a substitute of the defective or absent gene, which would be encapsulated in the bicelle contained in the liposome, to the target cells of the patient.

The high permeating capacity of the bicelles makes them appropriated structures as cosmetics by their demonstrated dermatologic properties due to the fact that they enhance a reinforce of the lipids present in the horny stratum, giving as a result an increase of the elasticity valves as well as an improvement of the characteristics of the biologic tissue (Barbosa-Barros, L.; Barba, C.; Cócera, M.; Coderch, L.; López-Iglesias, C.; de la Maza, A.; López, O. *Inter. J. Pharmaceut.* 2008, 352, 263) being useful to potentiate the repair of injured tissues because of skin aging, eczema, dryness, burns, cracks, spots and all those pathologies related with the lack of lipids in the cells of the horny stratum.

Additionally, the encapsulation within the liposomes of the invention of skin repair agents, vitamins, sun filters or other active principles could enhance the cosmetic applications of the liposomes.

Therefore, an aspect of the present invention refers to the use of the liposome of the invention, or a composition of the invention, or said composition that comprises as well an active principle for the preparation of the cosmetic product, in which the cosmetic has to be administered by the topic route.

It is to be understood as "cosmetic product" every substance or formulation for local application to be used in the different surface parts of the human body such as, without limitation, epidermis, head and skin hair systems, nails, lips and external genital organs or in the teeth and in the mucous systems of the mouth, for its cleaning, perfumation, modification of its aspect and protection and maintenance in satisfactory state and prevention or correction of body odours. The topic route uses skin and mucous systems for the administration of the cosmetic, including conjunctival nasal, oral and urogenital mucous systems and additionally head and skin hair systems, nails, lips and teeth.

Another aspect of the invention refers to the use of the liposome of the invention or the composition of the invention or said composition, which additionally comprises an active principle for its use as a medicament.

The liposome of the invention, as well as the composition of the invention, containing an active principle or not, may be used for the preparation of a medicament for the treatment, without limitation of disturbances of the skin, liver, kidney, heart, brain, bones, muscles, tissues associated to the gastrointestinal tract, urinary, respiratory, endocrine, nervous systems or auditive and ocular tissues.

One preferred embodiment refers to the use of the liposome of the invention or the composition of the invention or said composition which comprises additionally an active principle, for the preparation of a medicament for the treatment of disturbances of skin, nervous tissues or ocular tissues. In one still more preferable embodiment, the medicament adopts a form appropriate for the administration through the rachidian route or topic route through the conjunctival mucosa.

The term "adapted form" refers to the form to adapt the medicament of the present invention to permit its administration through the rachidian route or topic route or through the conjunctival mucosa.

Another possibility is for the medicament to adopt a form prepared for parenteral, skin, oral, epidural, sublingual, nasal, intracathecal, bronquial, lymphatic, rectal, transdermic administration or by inhalation. The form adapted for parenteral administration refers to a physical state which may permit its administration by injection, that is, preferable, in liquid state. Parenteral administration may be carried out by the intramuscular, intrarterial, intravenous, intradermic, subcutaneous or intraoseous route, however without limitation to these types of parenteral administration routes. The form adapted for the oral administration is selected within a list comprising, without limitation, drops, syrup, tisane, elixir, suspension, extemporaneous suspension, oral vials, tablets, capsules, granulates, seals, pellets, lozenges, pills, troches or lyophilized substances. The form adapted for the rectal administration is selected within a list comprising, without limitation, suppository rectal capsules, rectal dispersions or rectal ointments. The form adapted to transdermic administration is selected within the list comprising, without limitation, transdermic pads or iontophoresis.

Thus, a great number of applications are open in different fields for these bicellar nanostructures.

Another aspect of the invention refers to the pharmaceutical composition comprising the liposome of the invention, or comprising the composition of the invention, or comprising said composition which in addition comprises an active principle. In a preferred embodiment, the pharmaceutic composition comprises additionally at least one pharmaceutically acceptable excipient.

The term "excipient" refers to a substance assisting the absorption of the liposome of the invention, stabilizing said compound or assisting in the preparation of the pharmaceutic composition in the sense of contributing consistence or taste, flavour, texture and protection to the same making the compound more agreeable. Therefore, the excipients could have the function to maintain the components bounded as for example starches, sugars or celluloses, sweetening principles, colouring substances, a protection function of the medicament as for example to isolate the same from air and/or humidity, function of filling a tablet, capsule or any other form of presentation as for example dibasic calcium phosphate, disintegrating function to assist the dissolution of the components and its absorption within the intestine, without excluding any other type of excipients not mentioned in this paragraph.

The term "pharmacologically acceptable" refers to the fact that the compound is a permitted compound and it has been evaluated so that is does not cause harm to the organisms to which it is administered.

Within the active substances are to be considered, for example those above described both in a composition together with liposomes of the invention or encapsulated within the liposomes of the invention.

Another aspect of the invention refers to a method to obtain the liposome of the invention comprising:
 a. preparation of a dry lipidic film and an aqueous dispersion of bicelles,
 b. the hydration of the lipidic film obtained in the step (a) with the aqueous dispersion of bicelles obtained in the step (a),
 c. to isolate and/or to purify the product obtained in the step (b).

In a more preferred embodiment, the preparation of a dry lipidic film in step (a) comprises:
 i. the solution of lipids in an organic solvent in concentrations comprised within 5 and 30 mg/ml, and
 ii. to remove the organic solvent of the previous step.

In a more preferable embodiment, the preparation of the aqueous dispersion of bicelles in step (a) comprises:
 i. to solve in an organic solvent long chain phospholipids and short chain phospholipids with a molar concentration ratio of 1 to 10,
 ii. to remove the organic solvent of the previous step and rehydrate the product obtained with an aqueous solution until obtaining a concentration of lipids comprised between 15 and 25% weight/volume.

In a still more preferable embodiment, the long chain phospholipid is dimyristoyl-phosphatidilcholine or dipalmitoil-phosphatidylcholine and the short chain phospholipid is dihexanoil-phosphatidylcholine.

The final dispersion must be clear, for which reason the preparation method requires to follow various steps which have been optimized, including ultrasound treatments during a time comprised between 5 minutes and 5 hours to temperatures of 5-60° C. and a power application comprised between 100 and 600 W and an specific centrifugation process as described in the following paragraph, with the aim to separate/purify the liposomes of the invention from other lipidic aggregates which could have been formed.

An important step once the dry lipidic film is obtained, and the aqueous solution of bicelles is prepared and the lipidic film is hydrated with the solution of bicelles, is the purification of the obtained structures by means of centrifugation between 15000×g and 30000×g preferably 20000×g during periods of time comprised between 120 and 15 minutes, more preferably 45 minutes. More or less stringent conditions would lead to systems formed by blends of aggregates. Other purification/separation systems comprising dilutions, for instance, size exclusion resins, could provoke the transition of the non encapsulated bicelles to vesicles.

In the present description, as well as in the claims, the term "comprises" and its variations are not meant to exclude other technical characteristics such as morphology, topology, fluidity, viscosity, heterogeneity of the resulting structures, additives, components or steps. For the experts on the matter, other objects, advantages and characteristics of the invention will derive partly from the description and partly from carrying out the invention. The following figures and examples are provided as an illustration and are not meant to limit the present invention.

It shows the two types of phospholipids which a bicelle must have in each of its zones, being the end zones differentiated from the flat centre zone. In the zone designated (1) and in its opposed end, there is a higher rate of short chain fat acids in comparison to those with long chain. In the zone designated (2) and its surroundings, there is a higher concentration of long chain fat acids in comparison to those with short chain.

Figure 1:
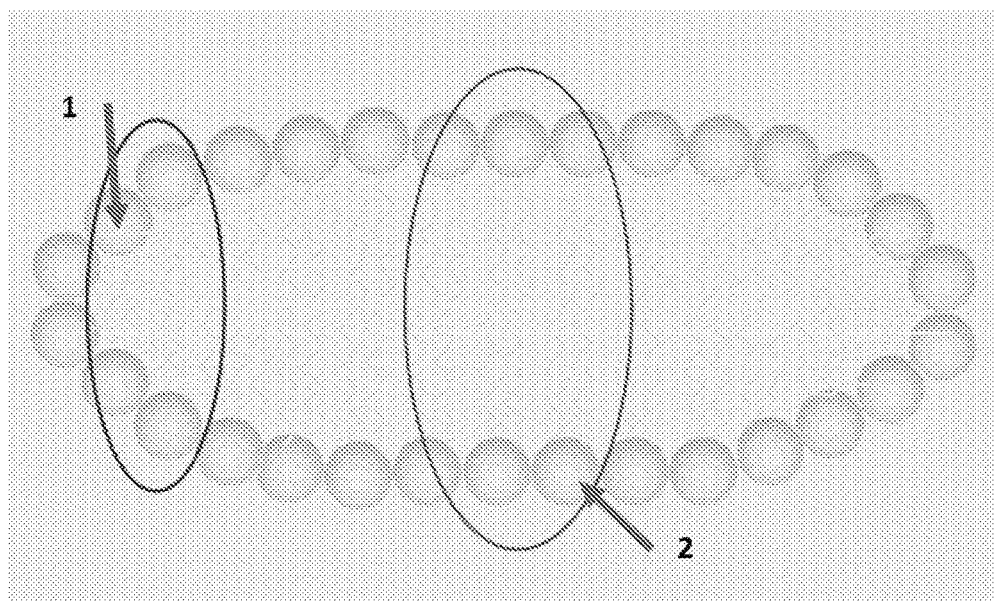
FIG. 1. Structure of a Bicelle.
Figure 2:
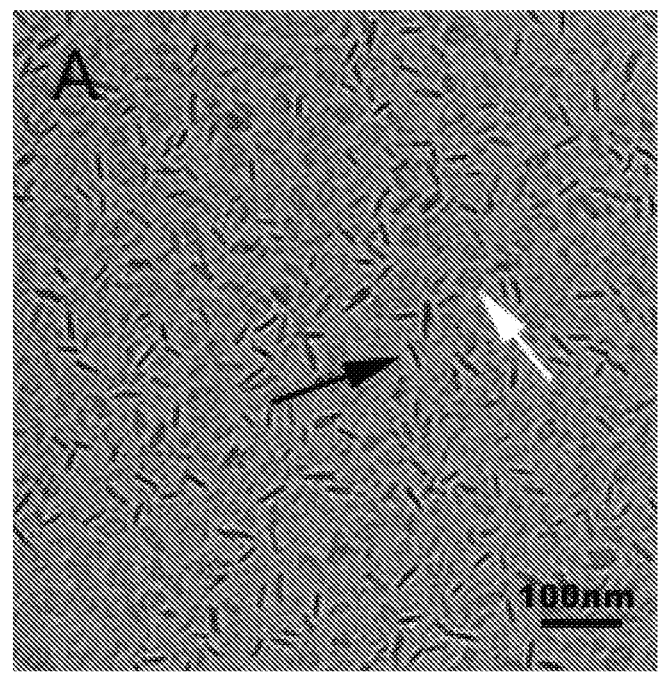
Figure 2:
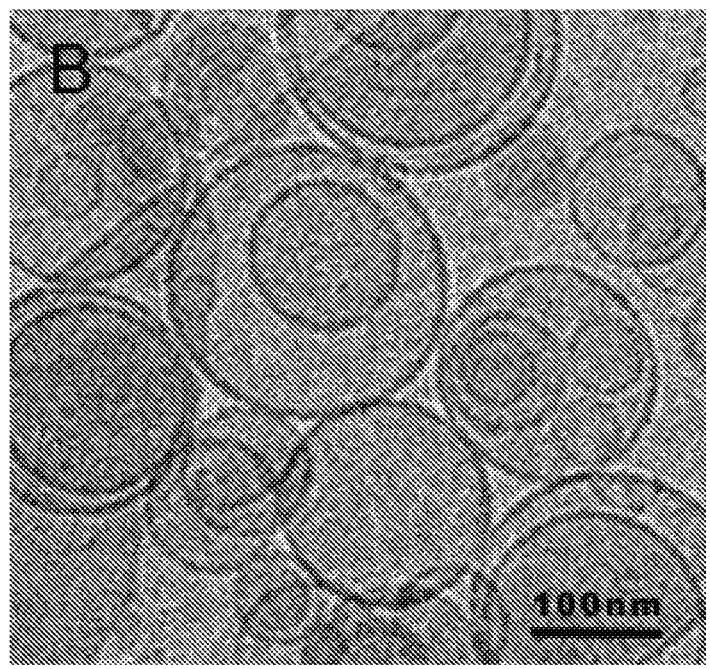

FIG. 2. Micro Photographs Showing Bicelle Samples Before Dilution (A) and After Dilution (B).

In FIG. 2A (bicelles) the bicelles are shown in all the projections: front (white arrow) and side (black arrow).

In FIG. 2B (diluted bicelles) spheric monolaminar vesicles are to be observed showing a broad variety of sizes (from 30 to 250 nm).

Figure 3:
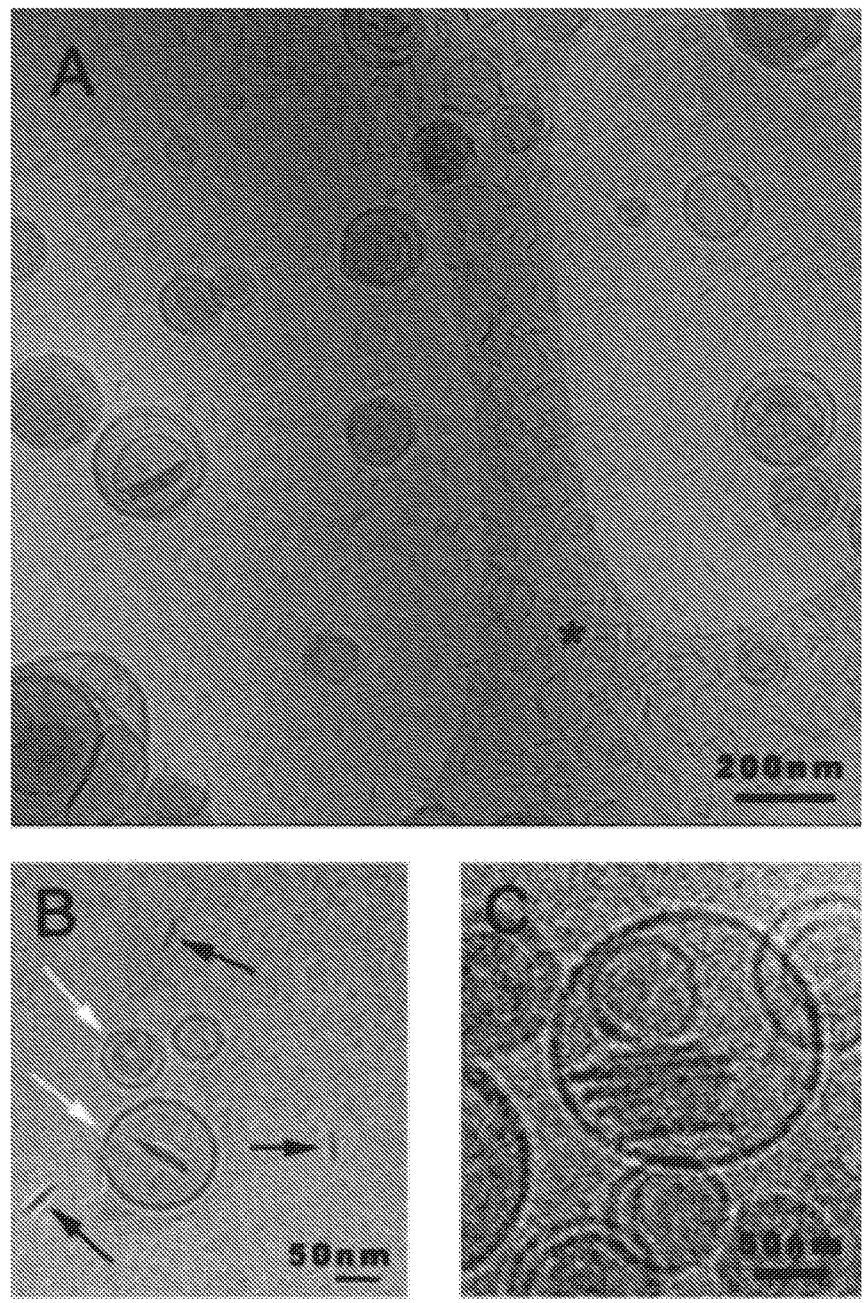

FIG. 3. Micro Photographs Obtained by Means of Cryo-TEM of Liposomes of the Invention (Liposomes and Bicelles).

In FIG. 3 two types of structures were observed: small size structures with approximately 20 nm and other with larger size of 100 to 200 nm.

FIG. 3A shows a general view of the sample of liposomes of the invention in which a great quantity of bicelles is to be seen. To be remarked is the great adhesion of the majority of the bicelles on the carbon (area shown in FIG. 3A with an astherisc). These bicelles show mainly the side projection.

FIG. 3B shows encapsulated bicelles in its two projections (white arrows) and non encapsulated bicelles (black arrows). Some of the encapsulated bicelles have an increase in size (around 100 nm) in comparison to non encapsulated bicelles (20 nm), as shown in FIG. 3A.

FIG. 3C shows stacked bicelles face to face within the liposomes.

Figure 4:
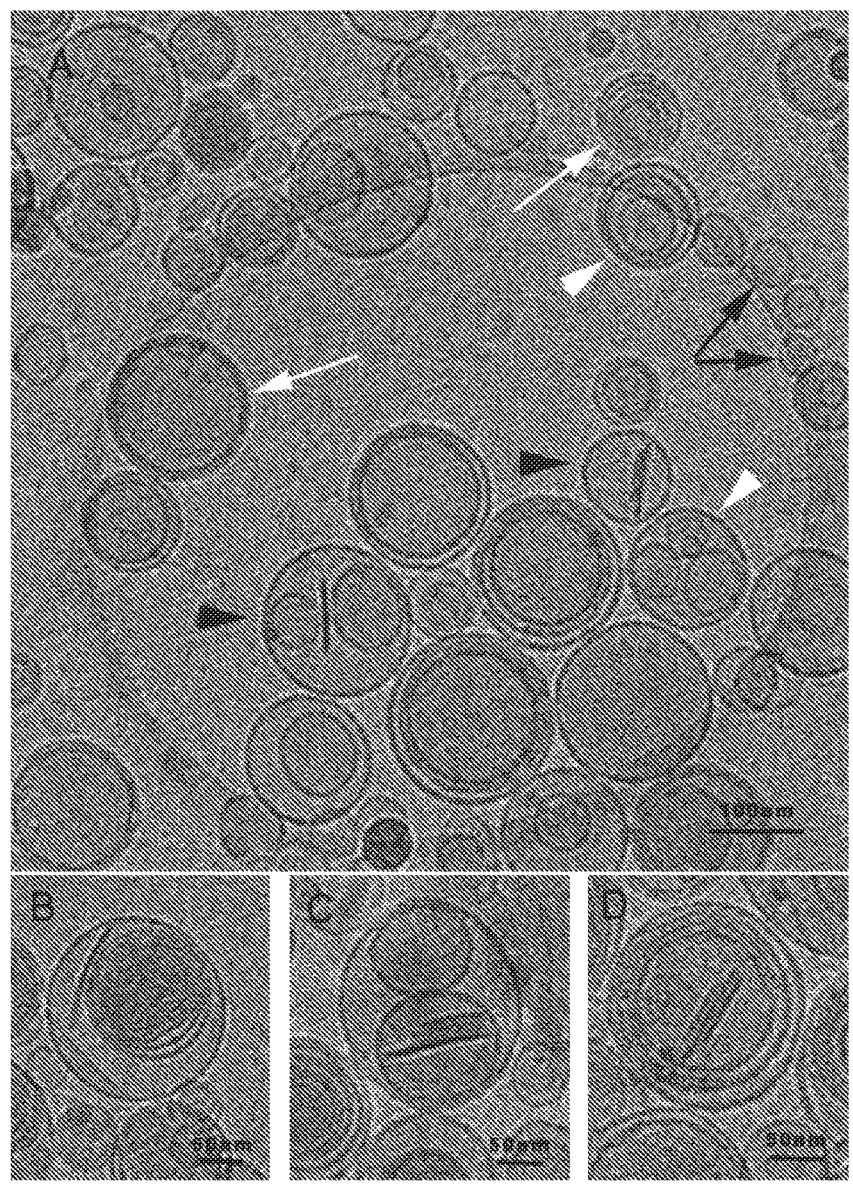

FIG. 4. Micro Photographs Obtained by Cryo-TEM of Diluted Liposomes of the Invention (Liposomes and Bicelles).

FIG. 4A shows a great variety of vesicles in the diluted sample: empty liposomes (black arrows); liposomes located within other liposomes called oligo-laminar vesicles (white arrow tip); multilaminar vesicles (white arrows) and liposomes with bicelles inside of liposomes of the invention (black arrow tip).

FIG. 4B shows multilaminar liposomes.

FIG. 4C shows accumulations of bicelles within liposomes as in the samples after dilution (FIG. 3C).

FIG. 4D shows in detail stacked bicelles within multilaminar liposomes.

Figure 5:
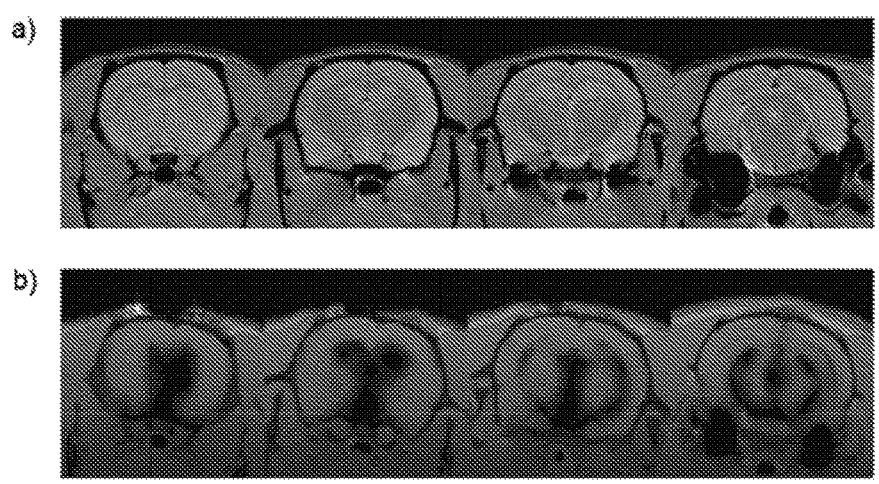

FIG. 5. Visualization by MRI of Intra-Ventricular Brain Injection of Bicelles containing gadodiamide.

FIG. 5A shows a frontal view of a healthy rat brain.

FIG. 5B shows the frontal view of the rat brain injected with the sample of bicelles containing gadodiamide.

Figure 6:
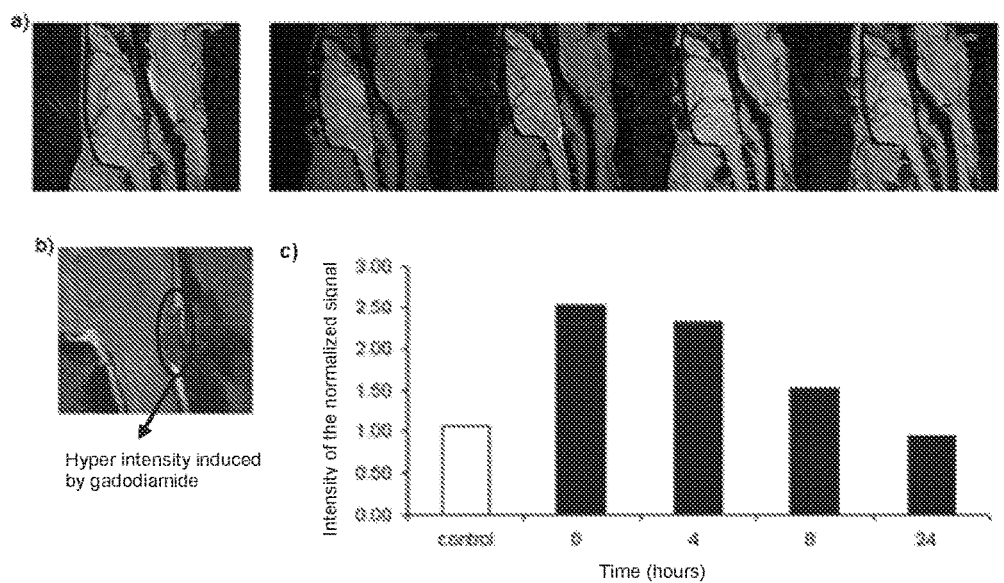

FIG. 6. Visualization by MRI of Intra-Ventricular Brain Injection of Bicelles Containing Gadodiamide, Encapsulated in Liposomes.

FIG. 6A shows a sagittal view of a healthy rat brain (first image), after injection with a sample of liposomes of the invention (liposomes internally containing gadodiamide bicelles) at 0, 4, 8 and 24 hours after injection (four following images).

FIG. 6B shows the hyperintensity induced by gadodiamide quantified representing the environment of an anatomic zone containing cerebrospinal fluid (CSF) at different moments of time. A detail of the concerned area.

FIG. 6C shows the intensity of the signal of the LCR (normalized in comparison to the muscle intensity) for a control rat (white bar) and for the rat injected with liposomes containing bicelles with gadodiamide (black bars) at different moments of time after the injection. It is an illustration to observe the evolution of hyperintensity with time.

Figure 7:
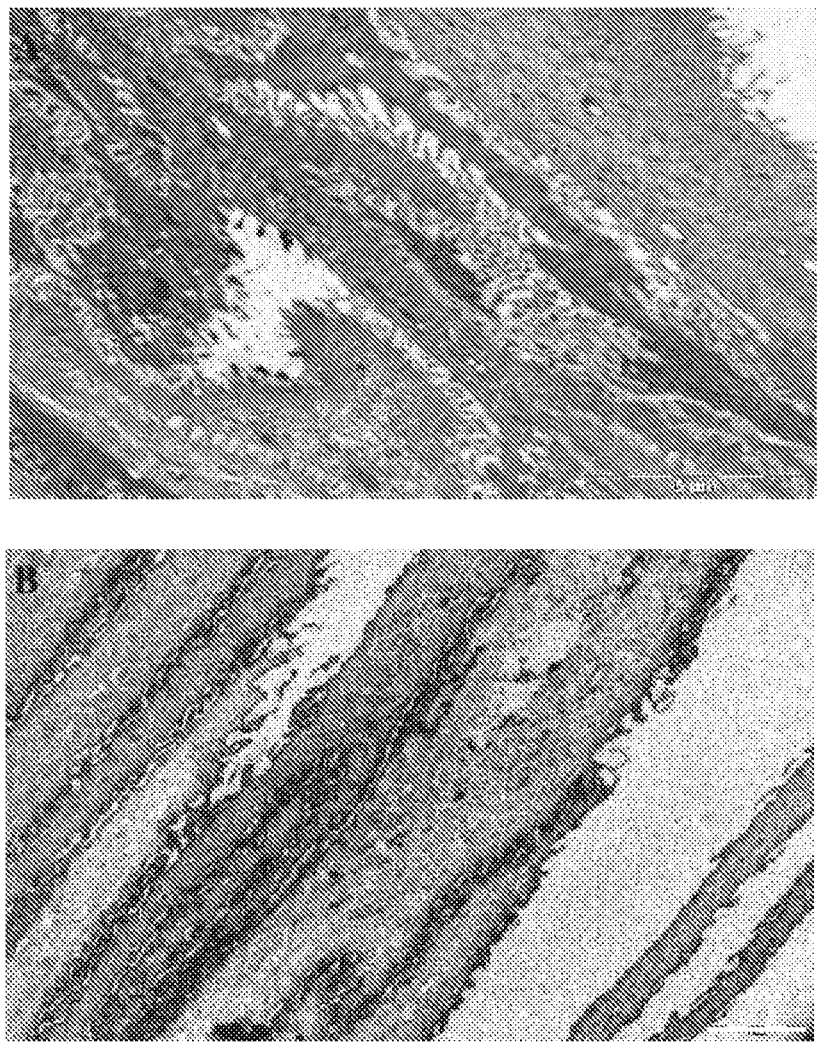

FIG. 7. Micro Photographs Obtained with TEM (Transmission Electronic Microscope) of the Oral Mucosa in Pigs.

FIG. 7A shows an image of the non treated mucosa and FIG. 7B shows the tissue after treatment with the liposomes of the invention containing nistatine. No structural changes may be observed which could be associated to damages in the tissue.

EXAMPLES

In the following, the invention will be illustrated by means of tests carried out by the inventors describing the preparation of the liposomes of the invention, its characterization by means of photonic correlation spectroscopy (DLS) and electronic transmission cryomicroscopy (Cryo-TEM) and the effect of the introduction of these systems in two Wistar rats by means of intra-ventricular brain injection by means of MRI visualization. In all the tests, the stability of the bicelles is challenged in diluted environments with the aim to use these nanostructures by means of systemic routes implying a high water content.

In these examples, the term "system" refers to the bicelles themselves or to the liposomes internally containing bicelles.

Example 1

Preparation of the Systems 1.1. Bicelles

The mix formed by DPPC/DHPC was selected for the preparation. The reason of this selection is due to the fact that within the operation periods at working temperature (from 25 to 37° C.) the bicelles composed by DPPC/DHPC do not show the changes observed in the bicelles composed by DHPC in combination with another long chain phospholipid. This fact may be explained because the DPPC has a Tm of 41° C., temperature which is substantially higher than the working temperature used in the present invention, which confirms that the transition in the structure of a bicelle takes place at temperatures which are above the transition temperature of the component lipids.

The samples were prepared mixing appropriate quantities of DPPC in powder form and a solution of DHPC in chloroform up to a molar ratio DPPC/DHPC of q=3.5 was obtained. Once the components were mixed, the chloroform was removed by means of a rotavapor and the resulting systems were hydrated with the solution of the gadodiamide paramagnetic marker up to reaching 20% (weight/volume) of the total lipid concentration. The bicelle solutions were prepared subjecting the samples to a number of cycles of sonication and freezing until the samples became clear.

1.2. Bicelles Encapsulated in Liposomes: Liposomes of the Invention.

The composition of the used liposomes was of 80% Lipoid S-100 and 20% cholesterol. These two components were mixed in chloroform and then a lipidic film was formed, the chloroform being removed by means of rotavapor. The formed film was hydrated with the bicellar solution previously prepared. The solution thus obtained was extruded three times through a 800 nm polycarbonate membrane. The liposomes dispersion was centrifuged for 45 minutes at 20000×g in a Heareus centrifuge with a JA-20 rotor. The floating layer was removed and the pellet was resuspended with NaCl 0.9% until the starting volume was obtained, with the aim to maintain the same lipid concentration. This procedure was repeated 3 times. Thus, it was possible to remove the encapsulated gadodiamide from that non encapsulated in the lipidic system.

Example 2

Characterization of the Systems

With the aim to evaluate the effect of the dilution in the systems, the samples were analyzed using the DLS and Cryo-TEM spectroscopic techniques before and after dilution. The first technique was used to determine the average size of the systems, while the second was very useful for the characterization of morphologic and dimensional aspects of the nanostructures and to provide a direct visualization of the samples of the lipids.

2.1. Photonic Correlation Spectroscopy (DLS)

The hydrodinamic diameter (HD) and the polydispersity index (PI) were determined by means of a Zetasizer Nano ZS90 apparatus (Malvern Systems, Southborough, Mass.). The DLS measurements take into account the Brownian movement of the particles and correlate this reading with the particle sizes. The relation between the particle size and its velocity due to the Brownan movement is defined by a Stokes-Einstein equation:

$$HD = kT/3\pi\eta D$$

In which: HD is the hydrodynamic diameter, D is the translational diffusion coefficient ($m^2/s$), k is the Boltzmann constant ($1,3806503 \times 10^{-23}$ $m^2$ kg $s^{-2}$ $k^{-1}$), T is the absolute temperature (K) and $\eta$ is the viscosity (mPa·s). The different sizes of the systems are determined by the detection and analysis of the scattered light when the 632 nm He/Ne laser beam passes through the sample.

The interpretation of the data was carried out taken into account the size distribution according to the intensity and volume of the scattered light. The use of this method, which considers that particles with different sizes diffuse different intensity of light is specially useful in samples having a high size heterogeneity. The measurements by DLS were carried out at 25 ad 37° C. with the purpose to study the characteristics of the systems at ambient and physiological temperatures.

The data obtained at ambient temperature are shown in table 1.

TABLE 1

HD and rate of the populations of particles analyzed by intensity and volume of scattered light.

|  |  | INTENSITY | | VOLUME | |
|---|---|---|---|---|---|
|  |  | HD (nm) | % Intensity | HD (nm) | % Volume |
| Bice | Peak 1 | 19.5 | 91.3 | 16.3 | 93.9 |
| Lipo Inv | Peak 1 | 92 | 100 | 11.9 | 100 |
| Bice Dil | Peak 1 | 255 | 88.4 | 256 | 3.6 |
|  | Peak 2 | 26.8 | 11.6 | 26.6 | 96.4 |
| Lipo Inv Dil | Peak 1 | 800 | 86.3 | 850 | 59.8 |
|  | Peak 2 | 72.4 | 13.7 | 68.7 | 40.2 |

Data obtained with the software provided by Malvern Instruments.

HD for DPPC/DHPC (Bice) bicelles were of 19.5 nm and 16.3 nm evaluated by intensity and volume, respectively, with a rate of scattered light exceeding 90% in both analysis.

The sample containing bicelles was diluted from 20% (initial concentration) to 0.07% (final concentration) to investigate the effect of dilution on the structure of the bicelles. Upon dilution of the sample (Bice Dil) two particle populations were observed in both analysis (by intensity and volume), one with a size around 26 nm and the other around 255 nm. The rates of the scattered light analyzed by intensity and volume were different. This is due to the fact that large and small particles contribute differently to the intensity of the scattered light. Thus, the larger particles scatter a larger intensity of light than small particles. For this reason, in systems with heterogeneous sizes, the analysis by intensity gave ground to a higher rate of large particles as is to be seen from table 1. The simultaneous analysis by volume revealed a higher rate of small particles (96.4%) than larger particles (3.6%) evidencing the predominating presence of small particles in the system although the intensity of scattered light for large particles (88.4%) was larger than for small particles (11.6%).

The PI values for bicelle systems were respectively 0.452 and 0.714 before and after dilution. Thus, after dilution of the sample, the size of the populations increased and the samples were more heterogeneous.

Anyway, it is necessary to take into account that in this technique the size of the particles approximates the size of an hypothetic sphere diffusing with the same velocity that the particle of the experiment. As the bicelle structure has disc form, the size of the particles obtained by DSL provides a relative measurement of the size of the structure. Therefore, these data must be understood taken into account the Cryo-TEM images analyzed in paragraph 2.2.

The results obtained by DSL for bicelles encapsulated within liposomes, (liposomes of the invention, Lipo Inv) are shown in table 1. The analysis by intensity and volume (both with a rate of scattered light of 100%) evidenced only one peak. The HD analyzed by intensity was of 92 nm and the corresponding to volume 11.9 nm. As above mentioned, these differences are due to the fact that the large particles (92 nm) scattered much more light intensity than the small particles (11.9 nm). It is for this reason that in the intensity analysis only one peak was observed which corresponds to the large particles. When analyzing the samples by volume, a great contribution of small particles was observed, which could hide the small contribution to the volume of the larger size particles for which reason only one peak was observed, which corresponded to the contribution of the small particles. Therefore, two types of structures were present although only one peak was observed for each analysis. In the following (paragraph 2.2) the obtained results by means of microscope are described to clarify this interpretation.

Upon dilution of the sample of liposomes of the invention (Lipo Inv Dil.) two peaks were clearly observed (table 1). In general, the structures became larger with diameters of 800 nm (86.3%) y 72.4 nm (13.7%) by intensity and 850 nm (59.8%) and 68.7 nm (40.2%) by volume. The PI values also increase from 0.420 to 0.612 before and after dilution, respectively.

The DLS data at 37° C. did not show any changes in comparison to the results at ambient temperature.

2.2 Electronic Transmission Cryomicroscopy (Cryo-TEM)

The liposomes and bicelles were visualized by the cryo-TEM method. A thin aqueous film was formed by extraction of the sample from the suspension placed on a grating. Carbon gratings were used for the purpose. After removing a part of the suspension from the grating, the suspension was dried by means of filter paper, a film of the sample remaining on the grating. These films were vitrified submerging the grating in ethane, which was maintained at its melting point with liquid nitrogen (according to the technique described in Honeywell-Nguyen, P. L.; Frederik, P. M.; Bomans, P. H.; Junginger, H. E.; Bouwstra, J. A. *Pharm Res* 2002, 19, 991) with the assistance of a Vitrobot device (FEI Company, Eindhoven, Holland) maintaining the samples before freezing at 100% humidity. The temperature at which the vitrification of the thin films started was ambient temperature. The vitreous samples were transferred to a Tecnai F20 microscope (FEI Company, Eindhoven, Holland) with a Gatan cryotransfert device (Barcelona, Spain). The display was carried out at 200 kV at a temperature comprised between −170° C. and −175° C. using the conditions for low density image.

In the images, a direct visualization of the bicellar structure is obtained. All measurements were obtained by DLS at ambient and physiologic temperatures (25° C. and 37° C.) and no size modification was detected by reason of the temperature. Given the fact that temperature had no effect on these systems, the cryo-TEM tests were carried out for cryo-set samples starting from ambient temperature. Some micrographs representing the samples before (sample of bicelles) and after (sample of diluted bicelles) the dilution, are shown, respectively, in FIGS. 2A and B.

The images confirmed the results obtained by DLS, evidencing that the size of the structures in the bicelles sample, around 20 nm in all cases, was smaller than the size of the structures in the samples of the diluted bicelles which evidenced sizes from 30 nm to 250 nm. In addition, the morphology of the particles changed as well with dilution (see FIG. 2). This fact coincides with the high PI values (0.714) observed by DLS. Thus, both DLS and microscopy show a transition of the system of bicellar discs to vesicles, which transition is provoked by the dilution.

With the aim to investigate the morphology of these systems, the samples of the liposomes and the diluted liposomes of the invention, were analyzed by cryo-TEM.

Also in this case, the samples for observation under microscope were only cryo-set at ambient temperature. Micrographs obtained by cryo-TEM are shown in FIGS. 3 and 4.

The variety of sizes between 70 nm and 600 nm shown in these images, confirms the high PI (0.612) in the sample of the diluted liposomes of the invention.

While the small structures correspond to disc-like bicelles, the larger structures correspond to unilaminar liposomes. These micrographs confirm the interpretation of the results of DLS for samples of the liposomes of the invention due to the fact that although only a peak was detected by means of volume and intensity analysis (table 1), two types of structures were observed. However, the results also show a high structural preservation of the encapsulated bicelles independently of the dilution process due to the fact that the samples of the diluted liposomes of the invention were only observed within the liposomes, no free bicelles being visualized (see FIG. 4).

Example 3

Incorporation of Different Substances into the Systems

The substances incorporated into the systems were as follows: iron (in the form of iron chloride to 50% concentration), ceramides (10 and 20%), caffeine (10%), gadodiamide (60%), cholesterol sulphate (20%), dyclophenac (1.16%) and fluphenamic acid (1%). The incorporation was made in the step of formation of the bicelles. Depending on the hydrophilic or lypophilic character of the substance, this was added together with the lipids forming the bicelle in the chloroform step or together with the hydration water. For these preparations, the following blends: DPPC/DHPC, DMPC/DHPC and DOPC/DHPC were selected. The DOPC is dioleoylphosphatidylcholine. The work was carried out with molar rates of the concentrations of both lipids between 2 and 3.5.

The samples were submitted between 10 and 50 sonication cycles in an ultrasound bath for a period of 5 minutes and 5 minutes of freezing until they became clear.

These bicelles, together with the substances internally contained were encapsulated in liposomes in the form described in example 1 and were characterized according to the methods described in example 2.

Example 4

Use of the Systems of the Invention in Products for Ocular Application

A compound showing therapeutic effect in the treatment of conjunctival mucous sensibilizations was incorporated into the systems of the invention as described in example 3. It was evidenced by means of microscope that this compound, which had been impossible to disperse using other emulsion systems (it always formed crystals of sizable dimensions) continued in dispersion without forming aggregates after being incorporated to the systems of the invention. This fact meant an appreciable success as the formation of crystals had prevented so far its use for ocular applications. The systems of the invention containing said compound were applied to the eyes of test animals and it was evidenced by means of microscope that no crystals have been formed upon establishing contact with the aqueous environment of the eyes.

In addition, stability and activity tests of the compound were carried out being ascertained that the compound maintained stability and activity after its incorporation to the systems of the invention.

Example 5

Experiments "In Vivo": Agent for Contrast Visualization by Means of Image Magnetic Resonance (MRI)

In addition, "in vivo" experiments were carried out to determine the stability of the new structures. The paramagnetic contrast agent gadodiamide was included in these systems. This agent was injected in the ventricular system in the brain of a rat and was visualized by magnetic resonance (MRI). It induced an hyperintensity which was quantified by means of the definition of a region of interest (ROI) in the compartment of the cefalorachidian liquid (LCR).

3.1. Animals

The MRI experiments were carried out with two Wistar rats (adult males with 250-275 g weight). The rats were conditioned to controlled temperature (21±1° C.) and humidity (55±10%) with 12 hours light/12 hours darkness cycles (light between 6:00 AM and 6:00 PM). Ad libitum food and water was administered during conditioning. All experiments were carried out following the rules of the "National Institute of Health Animal Protection Guidelines" and were approved by the authorities of the Local Bioethics Committee.

3.2. Sthereotactic Injections

The animals were previously anesthetized by means of 4% isofluorane in $O_2:N_2O$ 3:7 which concentration was reduced to 1% isofluorane during maintenance, being placed in an stereotactic apparatus (Stoelting, USA). The sagittal seam and the surface of the brain were used as references for anteroposterior (AP), middle-lateral (ML) and dorsum-ventral (DV) coordinates, respectively. An opening was made in the skull of the rat in order to inject the dispersion in the lateral ventricle with the following stereotactic coordinates: AP: −0.04 mm; ML: −0.12 mm; DV: −0.37 mm from the Bregma. 50 µl portions of an aqueous dispersion containing two different bicelle preparations (one formed by free bicelles and the other formed by the liposomes of the invention) mixed with gadodiamide were injected with a 100 µl Hamilton syringe equipped with a 32 G needle with an injection rate of 2 µl/minute.

After the injection, the needle was left in place during 5 minutes to prevent leaks. At the end of the surgery, the skin was sutured and the animal was transferred to the base of the scanning apparatus for obtaining RM images. The gadodiamide was injected together with the bicelle dispersion and also with the liposomes of the invention. The concentration of bicelles used for the injection was of 200 mg/ml. The researcher who carried out the stereotactic administration had an ample experience in this process.

3.3 Image Magnetic Resonance (MRI) "In Vivo"

RM sweepings were carried out under isofluorane anaesthesia with a 70/30 BioSpec horizontal scanner for animals (Bruker BioSpin, Ettlingen, Germany) with an internal diameter of 12 cm actively protected and with a gradient system (400 mT/m). The configuration ring consisted in a transmission/reception coil. The animals were placed in supine position on a plexiglass support with a nose cone for the administration of anaesthetic gases fixed with a bar to the teeth, stoppers for the ears and adhesive tape. Tripilot explorations were used for the precise placing of the head of the animal within the magnet. The head of the animal was placed so that approximately the centre of the brain coincided with the isocenter of the magnet. A sequence of sagittal axial T1 weighted images was carried out with a conventional flash (Fast Low Angle Shot images). The parameters of the exploration of the sagittal images were as follows: repetition time (TR)=350 ms, echo time (TE)=5.4 ms, 2 averages, thickness of the cut=1 mm, number of continuous cuts=15, field of vision (FOV)=4×4 $cm^2$, pattern=256×256×15 pixels, with a result of a space resolution of 0.156×0.156 mm in 1 mm thickness of the cut. In addition, T1 maps with axial orientation were carried out by means of RAREVTR (fast acquisition with improvement of the relaxation and variable sequence repetition time). The exploration parameters were as follows: TR=182.412 ms, 200 ms, 500 ms, 700 ms, 1000 ms, 1400 ms, 2000 ms, 3000 ms, 6000 ms, TE=10 ms, with a thickness of cut=1 mm, adjacent cuts=12, FOV=3×3 cm$^2$, pattern=128×128×12 pixels, resulting in a space resolution of 0.234×0.234 in 1 mm of the thickness of the cut. The acquisition of the images was carried out just after the injection and 4, 8 and 24 hours later.

3.4. Image Analysis.

A region of interest (ROI) was determined which was delimited according to the compartment of the cefalorachidian liquid (LCR) of each image to evaluate the increase of the signal produced by the gadodiamide. The signal was normalized and the paired off statistical analysis was carried out by means of T Student test (a value of p<0.05 was considered as meaningful).

When the injected substance consisted in free bicelles, five minutes after the end of the infusion of the bicelles both animals died, due to the drastic expansion to which the bicelles where submitted in all of the ventricular brain system of the rat. The MRI analysis was carried out "post mortem". FIG. 5 shows the front image of the brain of a healthy rat (A) and that of the specimen injected with the bicelles sample (B). It may be observed that the free bicelles showed a drastic expansion in all of the ventricular brain system of the rat which provoked death after the injection.

In case of injecting encapsulated bicelles, intraventricular brain (icy) injections where applied to rats with the aim to observe the increase of the intensity of the gadodiamide signal in CSF by the administration of the samples of liposomes of the invention. The rat was injected using the same experimental process. The animal was scanned immediately and also after 4, 8 and 24 hours. In contrast to the administration of the bicellar sample, the animal which received the sample of encapsulated bicelles or liposomes of the invention, survived. Said preparation did not show any apparently toxic consequences, an effect being observed depending on time with a maximum hyperintensity of the signal in the CSF in the analysis carried out immediately after the infusion of the preparation of liposomes of the invention and a progressive decrease of the signal with time. After 24 hours, the intensity was similar to the intensity which was found in healthy animals (control) (see FIG. 6).

Taking into account that the liposomes of the invention have a larger size than the bicelles in diluted mediums and even in this case permitted the survival of the animals, the fact that the intraventricular brain injection of the free bicelles was fatal for rats is explained by the fast and uncontrolled morphologic changes that these structures suffer when in contact with diluted mediums such as the cerebrospinal fluid. These sudden morphologic transitions are therefore the cause of a change of the composition of cerebrospinal fluid enhancing the expansion of the cerebroventricular system.

Example 6

Use of the Systems of the Invention for Antimycotics Treatment of Oral Mucosa

The nistatine molecule was incorporated to the systems of the invention as described in example 3. This compound has antibiotic antifungal activity and it is frequently used in skin and mucosa infections originated by Candida albicans fungus. The quantity of nistatine incorporated into the system of the invention was of the same order than in currently marketed products containing nistatine in suspension, that is, about 15.75 mg/ml. This circumstance evidenced to be a clear success as the systems of the invention have high water content and the difficulty to incorporate nistatine to this type of systems is well known (high water content).

The systems of the invention containing nistatine were applied to the oral mucosa region of pigs and after a three hour period of contact with the mucosa the quantity of nistatine retained in the tissue was determined by means of high performance liquid chromatography (HPLC). It was observed that all the nistatine applied was incorporated to the tissue, which is satisfactory when the objective is to treat fungus originated disturbances.

In addition, it was verified by means of a transmission electronic microscope that the tissue of the oral mucosa had not been significantly damaged by the effect of the treatment (FIG. 7).

It was also determined that the microbiologic activity of nistatine was not affected by its incorporation to the liposomes of the invention, the minimum inhibitory concentration (MIC) being of 16 µg/ml.

The invention claimed is:

1. A liposome, comprising in its internal aqueous medium, at least one bicelle;
   wherein said bicelle comprises phospholipids with a molar concentration ratio between long chain phospholipids and short chain phospholipids of 1 to 10; wherein the phospholipids comprise chains with a difference between the number of carbon atoms of any long chain and any short chain being between 5 and 25; and wherein the liposome has a diameter between 200 and 1000 nm, and in that the bicelle has a major axis with a length between 10 and 80 nm.

2. The liposome, according to claim 1, wherein said liposome comprises bicelles with a concentration from 5 to 25% in dry weight with respect to the final liposome.

3. The liposome, according to claim 1, wherein said liposome comprises lipids with an average transition temperature of 4 to 40° C.

4. The liposome, according to claim 1, wherein the long chain phospholipid is dimirystoil phosphatidylcholine or dipalmitoil phosphatidylcholine and the short chain phospholipid is dihexanoil phosphatidylcholine.

5. The liposome, according to claim 1, wherein the liposome additionally comprises at least one active principle.

6. The liposome, according to claim 1, further comprising a dye for the dyeing of biologic or textile fibers.

7. The liposome, according to claim 1, further comprising a pigment for the dyeing of biologic or textile fibers.

8. A composition comprising the liposome defined in claim 1.

9. The liposome defined in claim 1 for the elaboration of a cosmetic product.

10. The liposome defined in the composition of claim 8 for the elaboration of a cosmetic product.

11. The liposome defined in claim 1 for its use as medicament for the treatment of skin, nervous tissue or ocular tissues disturbances.

12. The liposome defined in the composition of claim 8 for its use as medicament for the treatment of skin, nervous tissue or ocular tissues disturbances.

13. The liposome according to claim 12, wherein the medicament adopts a form adapted for the administration by rachidean route or topic route or through the conjunctival mucosa.

14. A pharmaceutical composition comprising the liposome of claim 1, together with a pharmacologically acceptable excipient.

15. A pharmaceutical composition comprising the composition according to claim 8, together with a pharmacologically acceptable excipient.

16. A method for the preparation of the liposome defined in claim 1, comprising the steps of:
   (a) preparing a dry lipidic film and an aqueous dispersion of bicelles;
   (b) hydrating the lipidic film with the dispersion of bicelles, both obtained in step (a); and
   (c) isolating the product obtained in step (b) by centrifugation.

17. The method of claim 16, comprising isolating the product obtained in step (b) by centrifuging between 15000×g and 30000×g from 15 minutes to 120 minutes.

18. The method of claim 16, wherein preparing the dry lipidic film in step (a) comprises:
   (a) dissolving lipids in an organic solvent at concentrations between 5 and 30 mg/ml; and
   (b) eliminating the organic solvent of step (a).

19. The method of claim 16, wherein the preparation of the aqueous dispersion of bicelles of step (a) comprises:
   (a) dissolving within an organic solvent long chain phospholipids and short chain phospholipids with a molar concentration ratio between 1 and 10;
   (b) eliminating the organic solvent of step (a); and
   (c) rehydrating and dispersing of the product obtained with water up to a lipid concentration comprised between 15 and 25% weight/volume.

* * * * *